United States Patent [19]

Linn et al.

[11] Patent Number: 5,641,633
[45] Date of Patent: Jun. 24, 1997

[54] FLUORESCENCE POLARIZATION DETECTION OF NUCLEIC ACIDS

[75] Inventors: Carl Preston Linn, Durham; G. Terrance Walker, Chapel Hill; Patricia Anne Spears, Raleigh, all of N.C.

[73] Assignee: Becton, Dickinson and Company, Franklin Lakes, N.J.

[21] Appl. No.: 559,508

[22] Filed: Nov. 15, 1995

[51] Int. Cl.$^6$ ............................. C12P 19/34; C12Q 1/68
[52] U.S. Cl. ................ 435/6; 435/91.1; 435/91.2; 435/91.53; 536/24.3; 536/24.33; 536/25.32; 935/77; 935/78
[58] Field of Search ..................... 435/6, 91.1, 91.2, 435/91.53; 536/24.3, 24.33, 25.32; 935/77, 78

[56] References Cited

U.S. PATENT DOCUMENTS

| | | | |
|---|---|---|---|
| 5,188,934 | 2/1993 | Menchem et al. | 435/6 |
| 5,270,184 | 12/1993 | Walker et al. | 435/91.2 |
| 5,445,935 | 8/1995 | Royer | 435/6 |
| 5,455,166 | 10/1995 | Walker | 435/91.2 |

FOREIGN PATENT DOCUMENTS

| | | |
|---|---|---|
| 0 382 433 A2 | 8/1990 | European Pat. Off. |
| 0 678 581 A1 | 10/1995 | European Pat. Off. |
| 0 678 582 A1 | 10/1995 | European Pat. Off. |
| 2228998 | 4/1993 | United Kingdom. |
| WO92/18650 | 10/1992 | WIPO. |

OTHER PUBLICATIONS

Cook et al., Analytical Biochemistry 190:331–330 1990.

Walker et al., Nuc. Acids Res. 24(2):348–353 Jan. 15, 1996.

G. T. Walker, et al. "Strand Displacement Amplification —an isothermal, in vitro DNA amplification technique" Nucl. Acids Res. 20:1691–1696 (1992).

G. T. Walker, et al. "Isothermal in vitro amplification of DNA by a restriction enzyme/DNA polymerase system" Proc. Natl. Acad. Sci. USA 89:392–296 (1992).

A. Murakami, et al. "Fluorescent–labeled oligonucleotide probes: detection of hybrid formation in solution by fluorescence polarization spectroscopy" Nucl. Acids Res. 19:4097–4102 (1991).

Primary Examiner—Stephanie W. Zitomer
Assistant Examiner—Paul B. Tran
Attorney, Agent, or Firm—Donna R. Fugit

[57] ABSTRACT

The present invention provides methods for detecting amplified or unamplified nucleic acid target sequences at increased temperatures by changes in fluorescence polarization. The decrease in fluorescence polarization associated with hybridization of oligonucleotides at higher, more stringent, temperatures is overcome by including a double-stranded DNA binding protein in the assay. At elevated temperatures, the double-stranded DNA binding protein restores, and often enhances, the magnitude of the change in fluorescence polarization associated with single- to double-stranded conversion of an oligonucleotide probe or primer.

26 Claims, 1 Drawing Sheet

FLUORESCENCE POLARIZATION DETECTION OF NUCLEIC ACIDS

FIELD OF THE INVENTION

The present invention relates to methods for detecting nucleic acid target sequences and in particular to detecting such target sequences by changes in fluorescence polarization.

BACKGROUND OF THE INVENTION

Fluoresence Polarization (FP) is a measure of the time-average rotational motion of fluorescent molecules. It has been known since the 1920's and has been used in both research and clinical applications for sensitive determination of molecular volume and microviscosity. The FP technique relies upon changes in the rotational properties of molecules in solution. That is, molecules in solution tend to "tumble" about their various axes. Larger molecules (e.g., those with greater volume or molecular weight) tumble more slowly and along fewer axes than smaller molecules. There is therefore less movement between excitation and emission, causing the emitted light to exhibit a relatively higher degree of polarization. Conversely, fluorescence emissions from smaller fluorescent molecules, which exhibit more tumbling between excitation and emission, are more multiplanar (less polarized). When a smaller fluorescent molecule takes a larger or more rigid conformation its tumbling decreases and the emitted fluorescence becomes relatively more polarized. This change in the degree of polarization of emitted fluorescence can be measured and used as an indicator of increased size and/or rigidity of the fluorescent molecule.

In fluorescence polarization techniques, the fluorescent molecule is first excited by polarized light. The polarization of the emission is measured by measuring the relative intensities of emission (i) parallel to the plane of polarized excitation light and (ii) perpendicular to the plane of polarized excitation light. A change in the rate of tumbling due to a change in size and/or rigidity is accompanied by a change in the relationship between the plane of excitation light and the plane of emitted fluorescence, i.e., a change in fluorescence polarization. Such changes can occur, for example, when a single stranded oligonucleotide probe becomes double stranded or when a nucleic acid binding protein binds to an oligonucleotide. Fluorescence anisotropy is closely related to FP. This technique also measures changes in the tumbling rates of molecules but is calculated using a different equation. It is to be understood that polarization and anisotropy are interchangeable techniques for use in the present invention. The term fluorescence polarization is generally used herein but should be understood to include fluorescence anisotropy methods. In steady state measurements of polarization and anisotropy, these values are calculated according to the following equations:

$$P(\text{polarization}) = \frac{Ipa - Ipe}{Ipa + Ipe}$$

$$r(\text{anisotropy}) = \frac{Ipa - Ipe}{Ipa + 2Ipe}$$

where Ipa is the intensity of fluorescence emission parallel to the plane of polarized excitation light and Ipe is the intensity of fluorescence emission perpendicular to the plane of polarized excitation light.

As FP is homogenous, this technique is ideal for studying molecular interactions in solution without interference by physical manipulation. Fluorescence polarization is therefore a convenient method for monitoring conversion of single-stranded fluorescently labelled DNA to double-stranded form by hybridization (Murakami, et al. 1991. *Nucl. Acids Res.* 19, 4097–4102). The ability of FP to differentiate between single and double-stranded nucleic acid conformations without physical separation of the two forms has made this technology an attractive alternative for monitoring probe hybridization in diagnostic formats. European Patent Publication No. 0 382 433 describes fluorescence polarization detection of amplified target sequences by hybridization of a fluorescent probe to the amplicons or by incorporation of a fluorescent label into the amplification products by target-specific extension of a fluorescently-labeled amplification primer. PCT Patent Publication No. WO 92/18650 describes similar methods for detecting amplified RNA or DNA target sequences by the increase in fluorescence polarization associated with hybridization of a fluorescent probe.

Fluorescence polarization may be monitored in any of three different states: steady state, transient state, or dynamic state. In transient state FP, the excitation light source is flashed on the sample and polarization of the emitted light is monitored by turning on the photomultiplier tube after the excitation light source is turned off. This reduces interference from light scatter, as fluorescence lasts longer than light scatter, but some fluorescence intensity is lost. In steady state FP, excitation light and emission monitoring are continuous (i.e., the excitation source and photomultiplier tube are on continuously). This results in measurement of an average tumbling time over the monitoring period and includes the effects of scattered light. Dynamic FP may be monitored in either the time- or frequency-domain. Dynamic fluorescence techniques involve determining the lifetime of the fluorescent molecule in nanoseconds. The theory of dynamic fluorescence monitoring is described in "Principles of Fluorescence Spectroscopy" (Lakowicz, Plenum Press, 1983). Whereas steady state FP provides an average or "snapshot" of the fluorescence phenomena, dynamic FP allows one to observe the individual contributions of the fluorescent components in the system being studied. Use of these three fluorescence techniques is described by Kumke, et al. (1995. *Anal. Chem.* 67, 3945–3951), Devlin, et al. (1993. *Clin. Chem.* 39, 1939–1943), and Walker, et al. (1995. *Clin. Chem.* citation omitted).

Analysis of nucleic acids, and in particular detection of specific nucleic acid target sequences provides an extremely sensitive tool for diagnosis and identification of biological materials. Typically, nucleic acid target sequences are detected by specific hybridization to a labeled oligonucleotide probe. Several probe hybridization methods for detecting nucleic acid target sequences are known in the art (e.g., dot blots, Southern blots, Northern blots), but these are somewhat insensitive and are generally only applicable to samples containing relatively large amounts of the target sequence to be detected. Nucleic acid amplification techniques have greatly improved the sensitivity of target sequence detection by providing methods for specifically increasing the amount of target sequence prior to detection. Nucleic acid amplification methods can be grouped according to the temperature requirements of the procedure. The polymerase chain reaction (PCR; R. K. Saiki, et al. 1985. *Science* 230, 1350–1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad Sci. USA* 88, 189–193) and transcription-based amplification (D. Y. Kwoh, et al. 1989. *Proc. Natl. Acad. Sci. USA* 86, 1173–1177) require temperature cycling. In contrast, methods such as Strand Displacement Amplification (SDA; G. T. Walker, et al. 1992. *Proc. Natl. Acad. Sci. USA* 89, 392–396 and G. T. Walker, et al. 1992. *Nuc. Acids. Res.* 20, 1691–1696, and U.S. Pat. No. 5,455,166), self-sustained sequence replication (3SR; J. C. Guatelli, et al. 1990. *Proc. Natl. Acad Sci. USA* 87, 1874–1878), Nucleic Acid Sequence Based Amplification (U.S. Pat. No. 5,409,818), restriction amplification (U.S. Pat. No. 5,102,784) and the Qβ replicase system (P. M. Lizardi, et al. 1988. *BioTechnology* 6, 1197–1202) are isothermal reactions. Isothermal amplifications are conducted at essentially constant temperature, in contrast to the cycling between high and low temperatures characteristic of amplification reactions such as the PCR. The SDA reaction originally reported in the publications cited above ("conventional SDA") is typically conducted at a temperature between about 35° C. and 42° C., and is capable of $10^8$-fold amplification of a target sequence in about 2 hours. Recently, SDA has been adapted for higher reaction temperatures (about 45°–65° C.—"thermophilic SDA" or "tSDA"). tSDA is capable of producing $10^9$–$10^{10}$ fold amplification in about 15–30 min. at about 50°–60° C. In addition to increased reaction speed, there is a significant reduction in non-specific background amplification in tSDA as compared to conventional SDA.

Either unamplified or amplified target sequences may be detected by hybridization of a labeled oligonucleotide probe. This often requires separation of free and hybridized probe before the signal can be measured. However, monitoring changes in FP allows differentiation of free and hybridized probe without physical separation, thereby reducing operating steps and procedural complexity. As an alternative to probe hybridization, target amplification may be detected by generating double-stranded secondary amplification products from a single-stranded signal primer in a target amplification-dependent manner during the amplification reaction. Generation of secondary amplification products during target amplification is described and illustrated in published European Patent Application Nos. 0 678 582 and 0 678 581. In the process, a single-stranded oligonucleotide signal primer comprising a detectable label is converted to double-stranded form in a target amplification-dependent manner. Conversion of the signal primer occurs concurrently with the amplification reaction and may be detected as a change in FP when the label is fluorescent. The increase in FP associated with conversion of the signal primer to double-stranded form as a result of target amplification is approximately 20 mP using fluorescein or La Jolla Blue as the fluorescent label. When amplification is conducted at lower temperatures (e.g., about 35°–45° C.), the change in FP can be enhanced (e.g., to about 133–185 mP) by binding a double-stranded DNA binding protein to its specific binding sequence incorporated into the signal primer. In this system, enhancement is amplification-specific because protein binding can occur only when the binding sequence in the signal primer becomes double-stranded as a result of target amplification. At temperatures less than about 45° C., where the duplex is entirely double-stranded, enhancement of polarization is probably primarily the result of the DNA binding protein further slowing the tumbling time of the molecule.

The specificity of probe hybridization and/or amplification is increased at higher temperatures (e.g., 45°–75° C.). It is therefore desirable to combine the advantages of FP for detecting nucleic acid target sequences with elevated reaction temperatures. However, increased temperature was expected to be incompatible with FP detection. Many fluorescent labels are not stable at higher temperatures. In addition, higher temperatures promote "breathing" of the duplex and "fraying" of the ends, leading to increased single-strandedness. This increased single-strandedness near the fluorescent label, particularly at the end of the duplex, could significantly decrease the magnitude of the change in FP for the double-stranded form and potentially eliminate it at temperatures which are optimized for hybridization specificity. These concerns were supported by preliminary experiments evaluating the change in FP upon hybridization at 55° C. At this temperature there was no difference in polarization between the single-stranded and double-stranded forms of oligonucleotides. Further, FP is sensitive to sample viscosity, which is altered at higher temperatures. The effects of altered sample viscosity on the ability to use changes in FP for detection of nucleic acid target sequences at increased reaction temperatures were therefore uncertain.

SUMMARY OF THE INVENTION

In one embodiment, the present invention provides methods for detecting amplified or unamplified nucleic acid target sequences by changes in fluorescence polarization upon hybridization of a labeled probe at increased temperatures. In a second embodiment, the inventive methods are used for detection of target sequence amplification at increased temperatures. Amplification may be detected using methods in which double-stranded, fluorescent secondary amplification products are detected by an increase in FP. Preliminary experiments indicated that, at higher temperatures, increased single-strandedness of nucleic acid duplexes would severely reduce or eliminate the associated change in FP. However, it has been found that at increased temperatures double-stranded DNA binding proteins restore, and often enhance, the magnitude of the change in polarization associated with double-strandedness. It is believed that when hybridization or amplification is conducted at higher temperatures for improved specificity (e.g., about 45°–75° C.), binding of double-stranded DNA binding proteins to the double-stranded product may stabilize the double-stranded form and reduce the increased single-strandedness which contributes to the temperature-associated decrease in polarization.

DETAILED DESCRIPTION OF THE INVENTION

Figure 1:
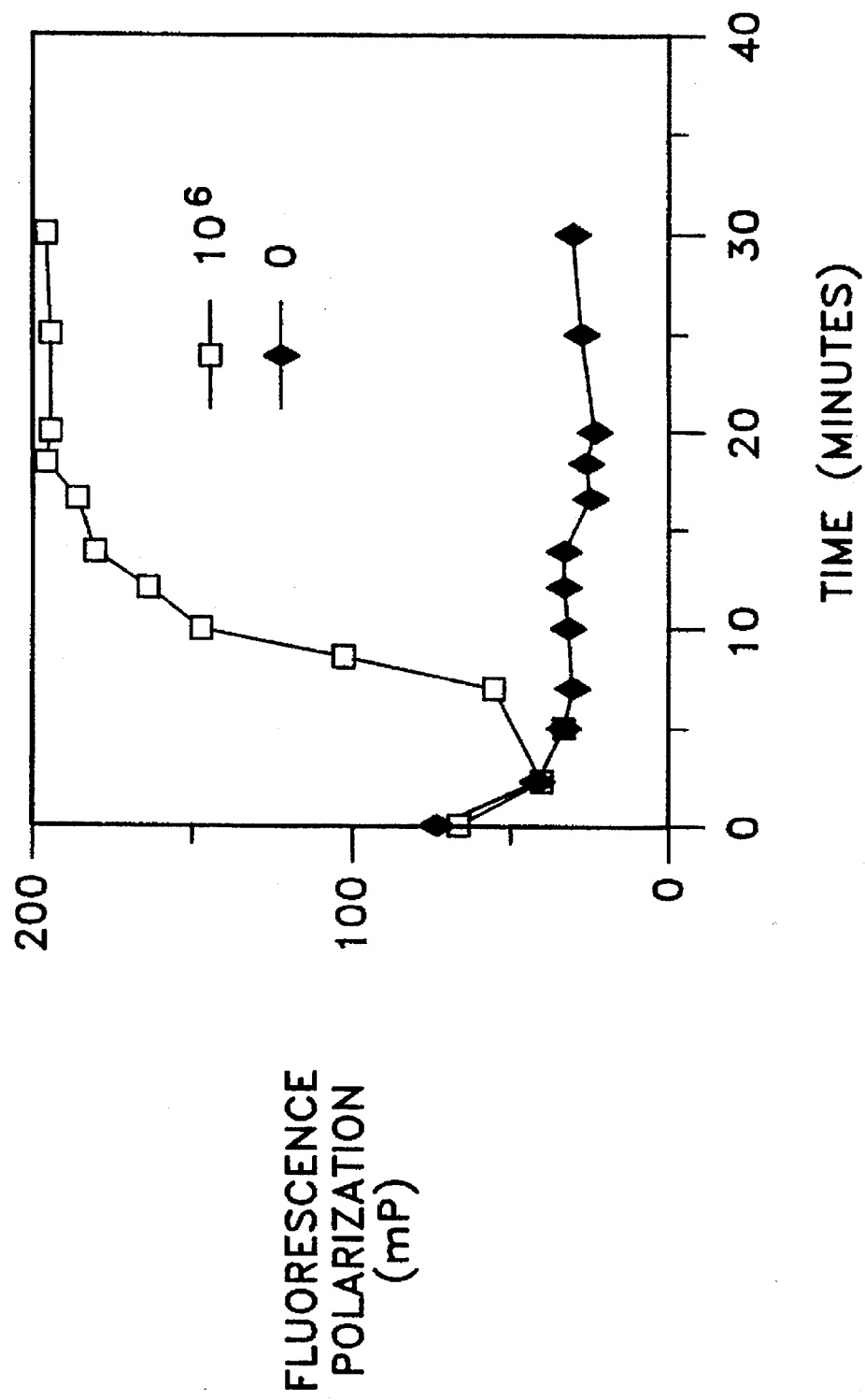
FIG. 1 illustrates real-time detection of target sequence amplification at 53.5° C.

When a nucleic acid target sequence is present in sufficient amounts, it may be detected by hybridization of an oligonucleotide probe comprising a detectable label. Many methods for direct detection by hybridization are known in the art. They include, for example, methods in which a single-stranded oligonucleotide probe is simply hybridized to the target sequence and detected by means of the detectable label as well as methods in which the hybridized probe is extended by polymerase to a diagnostic length prior to detection. To improve the specificity of hybridization and therefore the specificity of detection of the target sequence, it is desirable to hybridize the probe to the target at a temperature which is at or near the highest temperature at which efficient hybridization will occur. This temperature is partially dependent on the particular sequences of the probe and the target, but may easily be determined experimentally or by calculation for any desired target sequence and probe/primer. Hybridizing at higher temperatures increases stringency, minimizing non-specific cross hybridization of the probe to similar sequences and promoting hybridization predominantly to the target sequence of interest. Either amplified or unamplified target sequences may be detected by hybridization of a labeled probe. When hybridization of a probe comprising a fluorescent label is conducted at higher temperatures to improve specificity, the double-stranded structure may be stabilized by a sequence-specific or sequence-non-specific double-stranded DNA binding protein to maintain the change in FP associated with conversion of the single-stranded oligonucleotide to double-stranded form.

The improved specificity of primer hybridization at higher temperatures also makes it desirable to perform nucleic acid amplification reactions at temperatures close to the maximum for efficient amplification primer hybridization. This minimizes mispriming and as a result reduces the amount of non-specific background amplification. As discussed above, hybridization of a labeled probe to the amplified target sequence may be used for detection. However, recently developed methods for detection of target sequence in amplification reactions employ at least one signal primer (also referred to as a detector probe, EP 0 678 582 and EP 0 678 581). The signal primer is included in the amplification reaction to facilitate detection or monitoring of target amplification. During target amplification the single-stranded oligonucleotide (the signal primer) hybridizes to the target sequence and is extended by polymerase. The single stranded signal primer is rendered double-stranded as a result of target amplification to produce a secondary amplification product. Conversion of the single-stranded signal primer to double-stranded form in the secondary amplification product is an indication of target amplification, as secondary amplification products are not produced in the absence of target amplification. The decrease in the local mobility of the fluorophore which accompanies the change in probe conformation (primarily strandedness) results in a detectable change in correlation time (tumbling time) for the fluorescent label. Single- to double-stranded conversion of a signal primer comprising a fluorescent label may therefore be monitored by measuring changes in fluorescence polarization or fluorescence anisotropy.

At typical temperatures for isothermal nucleic acid amplification (e.g., about 35°–45° C.), conversion of a 5' fluorescein-labeled signal primer from single-stranded to double-stranded form produces a readily detectable increase in FP of about 20 mP. As described in EP 0 678 581 and EP 0 678 582, this increase may be enhanced by addition of a sequence-specific double-stranded DNA binding protein such as a restriction endonuclease, repressor protein, receptor binding protein, etc. By incorporating the appropriate recognition site for the double-stranded DNA binding protein into the signal primer, the recognition site becomes double-stranded as a result of target amplification, ensuring specific binding of the protein to secondary amplification products with enhancement of the amplification-specific change in FP. At lower temperatures, specific protein binding sequences are necessary to ensure that the protein binds only to secondary amplification products. This is believed to be due to the relatively high levels of mispriming by amplification primers at lower temperatures. In the absence of specific recognition sequences in the secondary amplification products, the double-stranded DNA binding protein binds to these non-specific amplification products in sufficient amounts to prevent detection of any amplification-specific enhancement in FP. In contrast, in the present invention either a sequence-specific or a sequence non-specific double-stranded DNA binding protein may be used to maintain the change in FP at higher, more stringent, amplification temperatures.

The changes in FP observed when the single-stranded probe or primer becomes double-stranded may be monitored on a variety of fluorometers appropriate for detection of the selected fluorescent label, including transient-state fluorometers (e.g., from Diatron), steady state fluorometers (e.g., from Jolley Instruments), or frequency-domain fluorometers (e.g., from SLM-Milton-Roy). Fluorescence polarization measurements may be taken post-hybridization or post-amplification (endpoint measurement). Alternatively, fluorescence polarization measurements may be taken during, or concurrently with, the hybridization or amplification reaction (real-time measurement). Real-time monitoring of fluorescence has significant advantages in that it provides an essentially immediate result, is quantitative, improves sensitivity (analysis of a change in slope is more accurate than a single endpoint), and the sample acts as its own internal standard. This last advantage is particularly important for analysis of clinical specimens, as sample viscosity may significantly affect endpoint readings.

Preliminary experiments suggested that the magnitude of the change in FP associated with conversion of nucleic acids from single- to double-stranded form would decrease with increasing temperature for end-labeled oligonucleotides. In nucleic acid hybridization studies, the change in FP ($\Delta MP$) was substantially unaffected at temperatures below about 45° C. However, $\Delta mP$ began to decrease at about 45° C., and was essentially absent as hybridization temperatures approached about 60° C. However, it was unexpectedly found that the change in FP upon hybridization could be maintained, and even enhanced, at temperatures of 45° C. or above when a double-stranded DNA binding protein was present. Further, probe hybridization studies indicated that the increase in FP associated with conversion of single-stranded signal primer to double-stranded secondary amplification product would be substantially eliminated at the reaction temperatures typical for thermophilic amplification reactions such as tSDA and PCR. However, it was unexpectedly found that increases in FP were maintained when generation of secondary amplification products was monitored in amplification reactions at about 45°–75° C. As the polymerases used to amplify nucleic acid targets are double-stranded nucleic acid binding proteins, Applicants believe that this phenomenon is due to sequence-nonspecific binding of the amplification polymerase to the secondary amplification products, producing an effect similar to that observed upon addition of a double-stranded DNA binding protein in the probe hybridization studies.

It also appears that the lower levels of mispriming associated with amplification at higher temperatures unexpectedly permit the use of sequence non-specific double-stranded DNA binding proteins to maintain or enhance changes in FP. FP detection of amplification in such amplification systems is therefore significantly simplified, as there is no need to engineer specific binding sequences into the signal primer, and the additional reaction component (a separate double-stranded DNA binding protein) is rendered optional. That is, in contrast to amplification at lower temperature, the enzymes already present for target amplification at higher temperatures (e.g., polymerase) also serve to maintain or enhance the target amplification-specific increase in FP. Of course, if desired, binding sequences for sequence-specific double-stranded DNA binding proteins as taught in EP 0 678 582 and EP 0 678 581 may be used in the present invention for monitoring changes in FP at increased temperatures in either target amplification or probe hybridization assays.

Binding of the double-stranded DNA binding protein may counteract the tendency of the duplex toward increased single-strandedness at higher temperatures, thereby stabilizing the double-stranded form. That is, binding of the protein may reduce end-fraying and breathing in the duplex. The stabilizing effect of these proteins has often been found sufficient to fully restore the increase in FP to at least the levels typical of lower assay temperatures. That is, double-stranded DNA binding proteins generally maintain at least the FP increase observed at about 37° C. when the amplification temperature or hybridization temperature is between about 45° C. and 75° C. As discussed below, the presence of the double-stranded DNA binding proteins in higher temperature assays may also enhance the magnitude of the change in FP.

The present disclosure uses SDA as an example of the methods of the invention in target amplification reactions, however, the invention may also be applied to any amplification method in which a target amplification-specific double-stranded secondary amplification product can be produced from a single-stranded probe or primer. This may be accomplished by using the amplification polymerase to displace a downstream signal primer. The inventive methods may therefore be used in isothermal amplification reactions other than SDA, e.g., 3SR, as the detection method is independent of whether the target sequence is RNA or DNA. In 3SR, target-dependent generation of double-stranded secondary amplification products occurs generally as it does for SDA. The T7 RNA polymerase used in 3SR lacks 5'–3' exonuclease activity and the degradative activity of reverse transcriptase is an RNAse H activity which is active only on RNA hybridized to DNA. Therefore, in the 3SR amplification scheme of Guatelli, et al. (1990. 87, 1874–1878), the signal primer may hybridize to the RNA target sequence and be displaced by extension of the 3' amplification primer ("A" in FIG. 1 of Guatelli, et al.). Alternatively, the signal primer may hybridize to the cDNA generated by reverse transcription at a position downstream from the 5' amplification primer ("B" in FIG. 1 of Guatelli, et al.). In either case, the extended signal primer is displaced by the polymerase when the upstream 3' ("A") or 5' ("B") amplification primer is extended. The opposite amplification primer then binds to the signal primer extension product and is extended, converting the labeled signal primer to double-stranded form. Signal primer extension products which include the T7 RNA polymerase promoter sequence are amplifiable by 3SR and provide a source of additional copies of the signal primer. The Transcription Mediated Amplification (TMA) and NASBA reactions are essentially the same as 3SR and would perform similarly to produce double-stranded target amplification-specific secondary amplification products with addition of a signal primer. Although 3SR and related amplification methods are currently conducted at temperatures below the thermophilic temperature range (i.e., at less than about 45°–75° C.), substitution of thermostable enzymes as necessary should allow fluorescence polarization detection of amplification under thermophilic conditions according to the present invention, as all of these amplification reactions include a sequence non-specific double-stranded DNA binding protein which would stabilize duplexes and maintain FP changes at the higher temperatures.

The inventive methods may also be applied to detecting amplification by the PCR, although fluorescence polarization measurements must be taken during the low temperature periods of the amplification cycle for "real time" monitoring of amplification. In PCR, the primer hybridization and extension step is typically conducted at about 60°–75° C. Using a 5'–3' exonuclease deficient polymerase (e.g., exo⁻Vent, exo⁻Pfu or the Stoffel fragment of Taq), extension of a PCR amplification primer hybridized to the target sequence displaces the extended downstream signal primer. The opposite PCR amplification primer hybridizes to the extension product of the signal primer and is extended, resulting in conversion of the single-stranded signal primer to double-stranded form. The double-stranded signal primer is amplifiable by hybridization and extension of one amplification primer and one signal primer in subsequent cycles, providing an additional source of double-stranded signal primer. The increase in fluorescence polarization or fluorescence anisotropy may then be detected after conclusion of the PCR under conditions in which amplification products remain double-stranded. Alternatively, secondary amplification products may be detected during PCR at the low temperature points of the cycling protocol (about 60°–75° C.), with the amplification polymerase serving to stabilize the secondary amplification product and maintain a detectable change in FP.

As an alternative to using a signal primer, the amplification primers of any of the foregoing amplification methods may be fluorescently labeled. This generates double-stranded fluorescently-labeled amplification products from the single-stranded amplification primers with an associated change in FP. Because background will be higher in this embodiment, sensitivity may be reduced as compared to use of a signal primer.

Any fluorescent molecule known in the art for labeling nucleic acids may be used in the methods of the invention, for example, fluorescein and fluorescein derivatives such as 5-(4,6-dichlorotriazin-2-yl) amino fluorescein (5-DTAF); eosin; rhodamines such as Texas Red, 6-carboxy-X-rhodamine (ROX) and tetramethylrhodamine; cyanine dyes such as thiazole orange, oxazole yellow and related dyes described in U.S. Pat. Nos. 4,957,870 and 4,888,867; pyrene; porphyrin dyes such as La Jolla Blue. The fluorescent label should be selected such that its fluorescent lifetime is comparable in magnitude to the correlation time being measured, taking into account that temperature, viscosity, and the size of the oligonucleotide to which the fluorescent dye is conjugated all affect tumbling time. For example, fluorescein (lifetime approximately 4 nanosec.) and LaJolla Blue (lifetime approximately 2 nanosec.) are both useful for correlation times of about 0.1–100 nanosec. If a nucleic acid binding protein is used in conjunction with the fluorescent label, the correlation time is generally increased. For example, correlation time for a free fluorescein label is about 0.2 nanosec. The correlation time increases to about 0.4 nanosec. when the fluorescein label is conjugated to a single stranded oligonucleotide and increases further to about 2 nanosec. when conjugated to a double-stranded oligonucleotide. When FP is enhanced by binding the fluorescein-labeled double-stranded oligonucleotide with a double-stranded DNA binding protein the correlation time increases again to about 20 nanosec. At temperatures less than about 45° C. there is essentially no end-fraying or breathing of the duplex nucleic acid. The increased correlation time in the presence of a DNA binding protein at these temperatures is therefore a reflection of the effect of the protein to further slow the tumbling time of the double-stranded molecule. La Jolla Blue (Devlin, et al. 1993. Clin. Chem. 39, 1939–1943) is particularly useful for labeling primers and probes for detection of nucleic acid target sequences in biological samples, as this dye absorbs and emits light in the near-infra red spectrum, a region of relatively low background fluorescence with clinical specimens (peak maxima at about 685 nm and 705 nm, respectively). It has also been found that 5-DTAF is superior to fluorescein for FP analysis when used as a label on nucleic acids. This label provides a significantly increased dynamic range as compared to fluorescein or La Jolla Blue and therefore improves the sensitivity of the FP assay.

The fluorescent label is covalently linked or conjugated to the probe or primer so as not to interfere with either emission of fluorescence from the label or hybridization of the probe or primer to the target sequence. As FP changes occur when the label is near or involved in a conformational change, the linkage should be in proximity to the site where the conformational change is expected. This may be, for example, at an internal site in the probe or primer, at the 5' end of the primer, or at either end of the probe. In general, the label is not linked to the 3' end of a primer, as the 3' end must be available for extension by polymerase. The fluorescent label is covalently coupled to the probe or primer via a linker or "tether" suitable for use in conjugating labels to oligonucleotides, e.g., amino-ethyl, amino-hexyl and aminopropyl linking arms (Applied Biosystems, Clontech, Glen Research, Devlin, et al., supra.). Other amino linkers are described in WO 92/18650. The label may also be conjugated to the oligonucleotide at C5 of pyrimidines or C8 of purines, as generally described by Goodchild, 1990. *Bioconj. Chem.* 1, 165. Fluorescein may be linked internally by synthesis of an oligonucleotide containing a phosphorothioate, and subsequent reaction with iodoacetamidofluorescein. Methods for linking 5-DTAF to oligonucleotides typically involve reaction of an amino-modified oligonucleotide with 5-DTAF in a $NaHCO_3/Na_2CO_3$ buffer. The labeled oligonucleotide is purified from unreacted excess dye by column chromatography and unlabeled oligonucleotide is removed to produce the final product. A more rigid tether, such as one containing double bonds, slows the tumbling time of the fluorescent label and allows measurement of longer correlation times.

It should be noted that when a change in FP is used for detection of nucleic acid hybridization or amplification in real-time (concurrently with conversion of the single-stranded oligonucleotide to double-stranded form during amplification or hybridization rather than after its completion), it is not necessary to "zero" the sample to compensate for background fluorescence as is required for endpoint measurements. This is because in FP detection of a change in polarization or a rate of change in polarization (not the magnitude of a change) indicates a positive result. Lower concentrations of fluorescently labeled signal primer or probe improve detection sensitivity by ensuring that a greater percentage of single-stranded signal primer or single-stranded probe is converted to double-stranded form for a given concentration of target. However, low signal primer or probe concentrations may result in saturation over a broad range of target levels when endpoint measurements are taken. End-point measurements of FP, taken after completion of the amplification or hybridization reaction, may therefore not be strictly quantitative with regard to the initial target levels. Monitoring FP in real-time overcomes the problem of saturation because samples containing higher target levels exhibit more rapid increases in FP values than those containing less target. Of course, the correlation between the rate of FP increase and initial target levels is valid only when comparing samples in which the rate of amplification or hybridization is essentially identical. For clinical specimens, which contain varying levels of inhibitors, the assay may not be strictly quantitative. For example, it may be difficult to differentiate a sample which contains a high amount of initial target and undergoes inefficient amplification from a sample which contains a low amount of initial target but undergoes amplification at a high rate. Nevertheless, real-time monitoring of FP values provides at least a semi-quantitative estimate of initial target levels. Quantitation may be improved by including an additional target sequence at a known initial concentration as an internal positive control (Walker, et al. 1994. *Nucl. Acids Res.* 22, 2670–2677), or assaying a parallel sample containing the positive control. The internal positive control not only provides an indication of general amplification or hybridization performance for a sample (ie., a control for false negatives), it also provides a standard for quantitating the amount of target in the sample.

EXAMPLE 1

A primary amine-labeled oligonucleotide was synthesized using AMINO-MODIFIER C6-TFA (Glen Research) on an ABI DNA Synthesizer Model 380B employing standard synthetic protocols (TAGAGTCTTCAAATATCAGAGCTTTACCTAACAA, SEQ ID NO: 1). The complementary oligonucleotide was also synthesized. The oligonucleotides were deprotected by heating with concentrated ammonium hydroxide at 55° C. for 15 hours and purified by standard PAGE techniques. SEQ ID NO: 1 (56 µL of a 150 µM solution) was mixed with 60 µL of $NaHCO_3/Na_2CO_3$ buffer (25 mM, pH 9). To this solution was added 10 µL of 40 mM 5-DTAF in DMF. The reaction was allowed to incubate at 37° C. for 72 hrs. in the dark. The labeled oligonucleotide was first purified from excess unreacted dye by column chromatography on a NAP-5 column (Pharmacia) equilibrated with 25 mM $NaHCO_3/Na_2CO_3$ buffer. Several 0.5 mL fractions were collected and the labeled oligonucleotide was found in Fraction 2. Fraction 2 was then further purified to separate labeled from unlabeled oligonucleotide using an Oligonucleotide Purification Cartridge (OPN, ABI) and conventional protocols. The final fraction was assayed for spectral purity on an HP 89532A spectrophotometer, scanning 240–600 nm. Optical densities were: $A_{260}$ 0.11273, $A_{494}$ 0.0215, $A_{260/280}$ 1.62, $A_{260/494}$ 5.25.

Three 1 mL samples were prepared in disposable borosilicate glass tubes (12×75 mm, Fisher) for analysis in the FPM-1 fluorometer. The first sample was a buffer blank (55 mM NaCl, 111 mM TRIS-HCl (pH 7.5), 0.7 mM $K_2HPO_4$ (pH 7.4), 1.1 mM EDTA, 0.7 mM β-mercaptoethanol, 0.27 µg/mL BSA, 0.02% TRITON X-100, 7% (v/v) glycerol), the second contained the single-stranded 5-DTAF labeled oligonucleotide, and the third contained the 5-DTAF labeled oligonucleotide hybridized to its complement. The FPM-1 maintained a temperature of 37° C. during FP measurements. At this temperature, the single-stranded 5-DTAF labeled oligonucleotide produced an FP reading of 121 mP and the double-stranded 5-DTAF labeled oligonucleotide produced an FP reading of 233 mP. This represents a change in polarization (ΔmP) of 112 mP upon conversion of the oligonucleotide from single- to double-stranded form.

The effects of temperature on ΔmP with conversion of SEQ ID NO: 1 to double-stranded form by hybridization were studied in the same buffer system. Four 2 mL samples were prepared: the buffer blank, 10 nM 5-DTAF single-stranded oligonucleotide, 10 nM 5-DTAF double-stranded oligonucleotide, and 10 nM 5-DTAF double-stranded oligonucleotide with a thermophilic double-stranded DNA binding protein (a thermophilic DNA polymerase). The complementary oligonucleotide was present in 50% excess in the double-stranded samples. The samples were incubated at 37° C. for 30 min. and initial FP readings were taken on the FPM-1 fluorometer. The samples were then transferred to 10 mm quartz fluorescence cuvettes (Spectrosil Far UV Quartz, Starna) and the temperature study was carried out on the SLM 8100 spectrofluorometer. The temperature (37° C., 50° C. and 55° C.) was controlled by a water bath (Lauda M-20) through the sample turret. The four samples were incubated in the turret for at least 1 hr. and then read with the excitation monochromator slits set at 8/4 mm, wavelength 494 nm and the emission monochromator slits set at 10/10 mm, wavelength 520 nm. For consistency, all polarization results were reported in the FPM-1 format (mP). The experiment was repeated at each temperature after addition of 275 units of the DNA polymerase in a volume of 5 μL.

The FPM-1 results for hybridization at 37° C., with (+) and without (−) the double-stranded DNA binding protein, are shown in Table 1

TABLE 1

| DS DNA Binding Protein | − | + |
|---|---|---|
| Single-stranded 5-DTAF labeled Oligonucleotide | 163 mP | 163 mP |
| Double-stranded 5-DTAF labeled Oligonucleotide | 231 mP | 353 mP |
| ΔmP | 68 | 190 |

Even at low hybridization temperature (37° C.), the double-stranded DNA binding protein provided nearly a three-fold enhancement in the magnitude of ΔmP with conversion of the single-stranded oligonucleotide to double-stranded form. Presence or absence of the binding protein had no effect on polarization of the single stranded oligonucleotide. However, FP of the double-stranded form was 122 mP higher in the presence of the DNA binding protein than in its absence, illustrating the specificity of the enhancement for double-stranded nucleic acids. At this hybridization temperature the hybridized duplex is entirely double-stranded, and the enhancing effect is therefore believed to be due to effect of the bound protein on the tumbling time of the molecule, adding to the increase in correlation time contributed by the single- to double-stranded conversion.

The SLM 8100 results for hybridization without double-stranded DNA binding protein at 37° C., 50° C. and 55° C. are shown in Table 2:

TABLE 2

| Temperature | 37° C. | 50° C. | 55° C. |
|---|---|---|---|
| Single-stranded 5-DTAF Oligonucleotide | 178 mP | 158 mP | 139 mP |
| Double-stranded 5-DTAF Oligonucleotide | 259 mP | 193 mP | 144 mP |
| ΔmP | 81 | 55 | 5 |

As the hybridization temperature increased, the polarization values of both the single-stranded and double-stranded oligonucleotides decreased. This may be partly due to the decrease in sample viscosity as temperatures increase. The decrease in FP was much more pronounced for the double-stranded oligonucleotide (115 mP vs. 39 mP between 37° C. and 55° C.), however, and this probably reflects increased single-strandedness due to the breathing and end-fraying which would not occur in the single-stranded oligonucleotide. The ΔmP therefore also decreased with increasing temperature and was only 5 mP at 55° C. This is not a significant change in polarization and is not a reliable indication of conversion to double-strandedness.

The SLM 8100 results for hybridization at 37° C., 50° C. and 55° C. with addition of DNA polymerase are shown in Table 3:

TABLE 3

| Temperature | 37° C. | 50° C. | 55° C. |
|---|---|---|---|
| Single-stranded 5-DTAF Oligonucleotide | 138 mP | 121 mP | 102 mP |
| Double-stranded 5-DTAF Oligonucleotide | 400 mP | 388 mP | 355 mP |
| ΔmP | 262 | 261 | 253 |

At all hybridization temperatures, addition of the double-stranded DNA binding protein significantly enhanced the change in polarization associated with single- to double-stranded conversion of the oligonucleotide. At 37° C., ΔmP was more than three-fold larger in magnitude in the presence of the binding protein than in its absence (compare Table 2 and Table 3). At higher hybridization temperatures (50° C. and 55° C.), not only was the previously observed loss of polarization overcome by the presence of the DNA binding protein, the magnitude of ΔmP was further enhanced to a level similar to that observed at 37° C. with protein enhancement. These results suggest that the DNA binding protein maintains or stabilizes double-strandedness to overcome the loss of polarization at higher temperatures. The DNA binding protein is also capable of enhancing ΔmP by slowing the tumbling time of the stabilized double-stranded form.

EXAMPLE 2

Additional experiments were conducted to confirm that the maintenance of FP at higher hybridization temperatures was a generalized effect of double-stranded DNA binding proteins and that the effect was also observed for other fluorescent labels. A 33-mer oligonucleotide containing a recognition site for the restriction endonuclease ApoI (GAATTC.) was synthesized and labeled at the 5' end with 6-FAM. The complement of the 33-mer was also synthesized. Four 100 μL samples containing 100 nM of the single-stranded 6-FAM oligonucleotide were prepared in 4 mM TAE, 50 mM NaCl pH 7.8. The complementary oligonucleotide (300 nM) was added to two of the samples. All samples were incubated at 37° C. for 30 min., after which they were diluted into 900 μL of 55 mM NaCl, 111 mM TRIS-HCl pH 7.5, 0.7 mM $K_2HPO_4$ pH 7.4, 1.1 mM EDTA, 0.7 mM β-mercaptoethanol, 27 μg/mL BSA, 0.02% TRITON X-100 and 7% glycerol. At this point in the procedure the concentration of the fluorescent oligonucleotide was 10 nM. The samples were then diluted 1:10 in the same buffer to give a final concentration of 1 nM fluorescent oligonucleotide in both the single- and double-stranded samples. The restriction endonuclease ApoI (2100 units, New England BioLabs) was added to one single-stranded sample and one double-stranded sample. All samples were initially incubated at 37° C. for 1 hr. and FP was measured on the FPM-1 fluorometer. They were then incubated at 56° C. for 1 hr. and re-read on the FPM-1.

The results are shown in Table 4:

TABLE 4

|  | mP at 37° C. | ΔmP | mP at 56° C. | ΔmP | mP at 56° C. + ApoI | ΔmP |
|---|---|---|---|---|---|---|
| SS | 43 |  | 33 |  | 33 |  |
| DS | 59 | 16 | 42 | 9 | 59 | 26 |

ApoI requires $Mg^{2+}$ to restrict double-stranded DNA. The absence of magnesium in this experiment allowed the enzyme to bind to its double-stranded recognition site in the hybridized oligonucleotides but prevented cleavage. The results demonstrate that sequence-specific double-stranded DNA binding proteins also stabilize and maintain ΔmP at higher hybridization temperatures. In this case, binding of the restriction endonuclease at 56° C. not only restored the change in FP associated with conversion of the oligonucleotide to double-stranded form but also enhanced it. The ΔmP at 56° C. was increased more than 50% as compared to the ΔmP observed for hybridization at 37° C.

Similarly, a 41-mer oligonucleotide containing a recognition site for the restriction endonuclease BsmFI (GTCCC.) was synthesized and labeled at the 5' end with 6-FAM. The complementary oligonucleotide was also synthesized. Six 100 μL samples were prepared as in the ApoI experiment, adding the complementary oligonucleotide to three of the samples. BsmFI (10 units, New England BioLabs) was added to one single-stranded sample and one double-stranded sample. In addition, 40 units of BsmFI were added to another of the single-stranded and double-stranded samples. The results are shown in Table 5:

TABLE 5

|  | mP at 37° C. | ΔmP | mP at 37° C. + BsmFI (10 units) | ΔmP | mP at 37° C. + BsmFI (40 units) | ΔmP |
|---|---|---|---|---|---|---|
| SS | 44.0 |  | 124.0 |  | 245.2 |  |
| DS | 63.2 | 19.2 | 158.8 | 34.8 | 303.9 | 55.7 |

|  | mP at 56° C. | ΔmP | mP at 56° C. + BsmFI (10 units) | ΔmP | mP at 56° C. + BsmFI (40 units) | ΔmP |
|---|---|---|---|---|---|---|
| SS | 35.2 |  | 43.7 |  | 142.7 |  |
| DS | 43.3 | 8.1 | 75.0 | 25.8 | 197.7 | 55.0 |

BsmFI is a Class IIs restriction endonuclease, which binds to its recognition site in double-stranded DNA but cleaves at an adjacent site. In this experiment, the BsmFI recognition site was sufficiently close to the end of the oligonucleotide to eliminate the cleavage site from the double-stranded molecule. This structure and the absence of magnesium, allowed the enzyme to bind but prevented restriction of the hybridized oligonucleotides. BsmFI was even more effective than ApoI for restoring and enhancing ΔmP at higher hybridization temperatures. At 56° C., in the presence of 40 units of BsmFI, ΔmP was almost three-fold larger in magnitude than at 37° C. in the absence of BsmFI. The degree of enhancement of ΔmP may also be related to the concentration of the double-stranded DNA binding protein.

A 27-mer oligonucleotide was synthesized and labeled at the 5' end with 6-ROX. The complement of the 27-mer was also synthesized. Four 100 μL samples were prepared as before and the complementary oligonucleotide was added to two of the samples. Bst polymerase (125 units, New England BioLabs) was added to one single-stranded sample and to one double-stranded sample. Fluorescence polarization was measured on the SLM 8100 fluorometer (Ex/Em 584/604). The results are shown in Table 6:

TABLE 6

|  | mP at 37° C. | ΔmP | mP at 56° C. | ΔmP |
|---|---|---|---|---|
| SS | 138.4 |  | 82.6 |  |
| DS | 160.4 | 22.0 | 86.8 | 4.2 |

|  | mP at 37° C. + Bst | ΔmP | mP at 47° C. + Bst | ΔmP | mP at 56° C. + Bst | ΔmP |
|---|---|---|---|---|---|---|
| SS | 197.0 |  | 184.7 |  | 148.1 |  |
| DS | 311.0 | 114.0 | 282.6 | 97.9 | 216.8 | 68.7 |

Bst DNA polymerase also restored and enhanced ΔmP at hybridization temperatures above 37° C. In this experiment, Bst increased the magnitude of ΔmP at 56° C. more than three-fold as compared to the change in polarization observed at 37° C. in the absence of polymerase. An approximately five-fold enhancement of ΔmP in the presence of the double-stranded DNA binding protein was observed even at 37° C. In addition, the magnitude of the change in polarization upon hybridization in the presence of the binding protein was more than 30 mP greater at 47° C. than at 56° C. Decreasing ΔmP with increasing temperature may reflect reduced viscosity of the medium and/or increased flexibility of the double-stranded molecule at higher temperatures. However, the tendency of the duplex toward increased single-strandness at higher temperatures may also begin to overcome the ability of the double-stranded DNA binding protein to stabilize the duplex and maintain the increase in polarization. Based on these and similar studies, Applicants predict that double-stranded DNA binding proteins will be effective to maintain useful changes in polarization for detection of hybridization and amplification up to about 75° C.

EXAMPLE 3

An IS6110 target sequence of *Mycobacterium tuberculosis* was amplified by tSDA, with inclusion of a signal primer for detection of amplification by generation of secondary amplification products. All oligodeoxynucleotides were synthesized using standard techniques and purified by gel electrophoresis. The 5'-fluorescein labeled signal primer was prepared using standard procedures and 6-FAM AMIDITE (Applied Biosystems, Inc.). The signal primer hybridized to nucleotide positions 985–1010 of the IS6110 element (D. Thierry, et al. 15 1990. *Nucl. Acids Res.* 18, 188) and had the following sequence:

5'-ATCCGTATGGTGGATAACGTCTTTCA    (SEQ ID NO:2)

The amplification and bumper primers were as follows, with the BsoBI recognition sequence shown in bold italics and the IS6110 target binding sequence underlined:

5'-CGATTCCGCTCCAGAC*TTCTCGGG*TCTACTG-   (SEQ ID NO:3, $S_1$)
AGATCCCCT
5'-ACCGCATCGAATGCATC*TCTCGGG*TAAGGCG-   (SEQ ID NO:4, $S_2$)
TACTCGACC
5'-CGCTGAACCGGAT    (SEQ ID NO:5, $B_1$)
5'-TCCACCCGCCAAC    (SEQ ID NO:6, $B_2$)

The samples were placed in disposable borosilicate glass test tubes (12×75 mM) and maintained at 37° C. during polarization measurement on the FPM-1 fluorometer. tSDA was performed in 100 μL samples with the final concentrations of reagents as follows: 35 mM K$_2$HPO$_4$ (pH 7.5), 3 mM TRIS-HCl (pH 7.9), 15 mM NaCl, 0.3 mM DTT, 10.5 mM MgCl$_2$, 1.4 mM each dGTP, dATP, TTP and dCTPαS, 0.1 mg/mL bovine serum albumin, 500 ng human placental DNA, 15 nM primer S$_1$, 6 nM primer S$_2$, 5 nM each primers B$_1$ and B$_2$, 320 units BsoBI (New England Biolabs), 8 units Bca (Panvera), 5 nM 5'-fluorescein labeled signal primer and the amounts of M. tuberculosis DNA indicated in Table I. The samples were initially prepared in 70 μL of 50 mM K$_2$HPO$_4$ (pH 7.5), 10.7 mM MgCl$_2$, 2 mM each dGTP, dATP, TTP and dCTPαS, 0.14 mg/mL bovine serum albumin, 21.4 nM primer S$_1$, 85.7 nM primer S$_2$, 7.1 nM each primers B$_1$ and B2, and 7.1 nM 5'-fluorescein labeled signal primer. Varying amounts of target were then added to each sample in a 10 μL aliquot of 10 mM TRIS-HCl pH 7.9, 10 mM MgCl$_2$, 50 mM NaCl, 1 mM DTT with 500 ng of human placental DNA. These 80 μL samples were denatured by heating for 2 min. in a boiling water bath and equilibrated for 3 min. at 60° C. for primer annealing. BsoBI and exo$^-$ Bca polymerase were diluted together to 16 units/μL and 0.4 units/μL, respectively, in 10 mM TRIS-HCl pH 7.9, 10 mM MgCl$_2$, 50 mM NaCl, 1 mM DTT and added in a 20 μL aliquot to each 80 μL SDA sample equilibrated at 60° C. After mixing, SDA was allowed to proceed for 15 min. at 60° C. and was then terminated by addition of 6 μL of 0.5M EDTA. The samples were diluted with 0.9 mL of 55 mM NaCl, 111 mM TRIS-HCl (pH 7.5), 0.7 mM K$_2$HPO$_4$ (pH 7.4), 1.1 mM EDTA, 0.7 mM β-mercaptoethanol, 27 μg/mL bovine serum albumin, 0.02% TRITON X-100, 7% (v/v) glycerol. Fluorescence polarization was measured after equilibration at 37° C. A preparation of an exonuclease deficient Klenow fragment of E. coli polymerase I (United States Biochemical) was then added (5 μL of a 5 units/μL stock solution) and fluorescence polarization was recorded a second time at 37° C.

The signal primer exhibited a target amplification-dependent increase in fluorescence polarization as shown in Table 7 (mP):

TABLE 7

| Number of M. tuberculosis genomes | | | | |
|---|---|---|---|---|
| 1000 | 100 | 10 | 1 | 0 |
| 114 (154) | 108 (136) | 79 (95) | 62 (68) | 57 (60) |

* values in parentheses are post polymerase addition

Samples containing higher input target exhibited higher polarization values, while the negative control (0 input target) exhibited a polarization value comparable to that of the single-stranded signal primer. Amplification of ten M. tuberculosis genomes was clearly detectable over the negative control and amplification of one genome was slightly increased above background.

Upon addition of the polymerase and remeasurement of fluorescence polarization, FP values were considerably enhanced for the amplified samples which contained M. tuberculosis DNA, resulting in increased assay sensitivity. As FP was measured at 37° C., this is probably primarily because binding of the polymerase to the double-stranded secondary amplification product further slows the tumbling time of the fluorescent label on the signal primer. There was essentially no increase in FP in the sample which did not contain the target. Enhancement of ΔmP in tSDA with addition of a polymerase was unexpected, as conventional SDA requires a sequence-specific binding protein in order for enhanced FP to be observed. This may be due to the higher incidence of mispriming at the lower operating temperature of conventional SDA. In contrast, the higher operating temperature of tSDA appears to reduce background amplification to a level which eliminates the need for sequence-specificity in the DNA binding protein. That is, at the completion of tSDA the double-stranded DNA present is predominantly target-specific. A double-stranded DNA binding protein which does not specifically bind to the secondary amplification products can be used because conditions are such that background amplification is essentially absent. Any double-stranded DNA specific binding protein should therefore be effective to enhance the change in FP under the conditions of tSDA.

Evidence of enhancement of the change in FP was evident even before addition of the exo$^-$ Klenow polymerase. Similar effects were observed in mock SDA reactions where the signal primer was hybridized to a complementary oligodeoxynucleotide. In the absence of BsoBI and Bca, there was an increase in FP from 55 mP to 70 mP upon hybridization. Addition of BsoBI and Bca resulted in a hybridization-associated increase in FP to about 125 mP. These results were unexpected because conventional SDA, with polarization similarly measured at 37° C., did not show any enhancement in the absence of added DNA binding protein. The results of the mock SDA reactions, and the observation of mP values greater than 70 mP prior to addition of polymerase in the high target samples in Table 7, suggest that double-stranded DNA binding proteins already present in the amplification reaction also serve to enhance the change in FP. Further, FP begins to decrease if tSDA is extended beyond the time of maximum target amplification (generally about 15 min.). This is also the point of the amplification reaction at which non-specific background products begin to increase.

EXAMPLE 4

Thermophilic SDA reactions to amplify a target sequence in the Chlamydia trachomatis elementary body (EB) were performed in a 1 mL volume containing 5 mM MgCl$_2$ (Sigma), 0.2 mM each dGTP, dATP, TTP (Pharmacia, 1.4 mM dCTPαS (United States Biochemicals), 20 μL/mL non-acetylated bovine serum albumin (New England BioLabs), 1 ng/μL human placental DNA (Sigma), 40 mM K$_2$HPO$_4$ pH 7.6, 5% (v/v) glycerol, 3% (v/v) DMSO, 0.75 μM primer S$_1$, 0.1875 μM primer S$_2$, 10 nM 5-DTAF labeled signal primer, 0.075 μm primers B$_1$ and B$_2$, 3.2 units/μL BsoBI (New England BioLabs), 0.25 units/μL exonuclease deficient Bst DNA polymerase (Molecular Biology Resources) and 0 or $10^6$ Chlamydia elementary bodies (EB's). The reaction containing no target also contained 10 μL 0.5M EDTA to ensure that no amplification could occur.

Prior to the addition of BsoBI, Bst polymerase, BSA and MgCl$_2$ the reactions were heated at 95° C. for 5 min. to denature the target DNA. After denaturing the target, the samples (800 μL) were transferred to a cuvette in an SLM 8100 fluorometer and allowed to equilibrate at 53.5° C. for 10 min. Amplification was initiated by adding 200 μL of enzyme mix (100 μL 50 mM MgCl$_2$, 20 μL 1 mg/mL BSA, 20 μL 25 units/μL Bst polymerase, 20 μL 160 units/μL BsoBI and 40 μL 1X NEB2 (New England BioLabs). FP was monitored every 2 min. using L-optics through a monochromator. The excitation wavelength was 494 nm and the emission wavelength was 520 nm, which are optimal for fluorescein and 5-DTAF.

The results are shown in FIG. 1, which illustrates an increase in FP with time in the reaction containing target ($10^6$ EB's). The maximum ΔmP was about 161.4 in this reaction and the target is detectable in about 6–8 min. at this initial concentration. The reaction containing no target and EDTA shows no increase in FP. The ΔmP was similar when the reactions were monitored on the FPM-1 fluorometer, although the polarization values were different.

Based on the results of probe hybridization studies conducted at comparable temperatures, it was unexpected that significant increases in polarization would be detectable in thermophilic amplification reactions such as tSDA. Applicants believe that under these reaction conditions the polymerase used for amplification also functions as a stabilizer of the double-stranded secondary amplification product, thus reducing or preventing the increase in single-strandedness typical of elevated amplification temperatures. Stabilization of the double-stranded structure appears to maintain, and in some cases to even enhance, the amplification-dependent increase in polarization at higher temperatures.

What is claimed is:

1. A method for detecting a target nucleic acid sequence comprising:
   a) converting a single-stranded oligonucleotide comprising a fluorescent label to double-stranded form by hybridizing the single-stranded oligonucleotide to the target sequence at about 45°–75° C.
   b) binding a double-stranded DNA binding protein to the double-stranded form at about 45°–75°; and
   c) detecting the target sequence by detecting a change in fluorescence polarization resulting from conversion of the single-stranded oligonucleotide to the double-stranded form with the double-stranded DNA binding protein bound thereto at about 45 °–75° C.

2. The method of claim 1 wherein the single-stranded oligonucleotide is a probe which is converted to double-stranded form upon hybridization to the target sequence.

3. The method of claim 2 wherein the hybridized probe is extended on the target sequence prior to detecting the change in fluorescence polarization.

4. The method of claim 1 wherein the single-stranded oligonucleotide is hybridized to the target sequence at about 50°–60° C.

5. The method of claim 1 wherein the double-stranded DNA binding protein binds to a specific recognition sequence in the double-stranded form of the oligonucleotide.

6. The method of claim 5 wherein the double-stranded DNA binding protein is a restriction endonuclease.

7. The method of claim 1 wherein the double-stranded DNA binding protein binds sequence non-specifically to the double-stranded form of the oligonucleotide.

8. The method of claim 7 wherein the double-stranded DNA binding protein is a polymerase.

9. The method of claim 1 wherein the fluorescent label is 5-(4,6-dichlorotriazin-2-yl) amino fluorescein).

10. The method of claim 1 wherein the change in fluorescence polarization is detected in real-time as the single-stranded oligonucleotide is converted to double-stranded form.

11. The method of claim 1 wherein the change in fluorescence polarization is detected as an endpoint measurement upon completion of conversion of the single-stranded oligonucleotide to double-stranded form.

12. A method for detecting amplification of a target nucleic acid sequence comprising:
   a) amplifying the target sequence at about 45°–75° C. such that a single-stranded oligonucleotide primer comprising a fluorescent label is converted to double-stranded form as a result of target sequence amplification;
   b) binding a double-stranded DNA binding protein to the double-stranded form at about 45°–75° C.; and
   c) detecting target sequence amplification by detecting a change in fluorescence polarization resulting from conversion of the single-stranded primer to the double-stranded form with the double-stranded DNA binding protein bound thereto at about 45°–75° C.

13. The method of claim 12 wherein the change in fluorescence polarization is detected in real-time as the single-stranded primer is converted to double-stranded form.

14. The method of claim 12 wherein the change in fluorescence polarization is detected as an endpoint measurement upon termination of target sequence amplification.

15. The method of claim 12 wherein the single-stranded primer is a signal primer.

16. The method of claim 12 wherein the double-stranded DNA binding protein binds to a specific recognition sequence in the double-stranded form of the primer.

17. The method of claim 16 wherein the double-stranded DNA binding protein is a restriction endonuclease.

18. The method of claim 12 wherein the double-stranded DNA binding protein binds sequence non-specifically to the double-stranded form of the primer.

19. The method of claim 18 wherein the double-stranded DNA binding protein is a polymerase.

20. The method of claim 12 wherein the fluorescent label is 5-(4,6-dichlorotriazin-2-yl) amino fluorescein).

21. The method of claim 12 wherein the single-stranded primer is an amplification primer.

22. The method of claim 19 wherein the polymerase is a polymerase used to amplify the target sequence.

23. The method of claim 22 wherein the single-stranded oligonucleotide primer is a signal primer which is converted to double-stranded form in a target amplification-dependent manner.

24. The method of claim 22 wherein a second double-stranded DNA binding protein is bound to the double-stranded form prior to detecting the change in fluorescence polarization.

25. The method of claim 22 wherein the target sequence is amplified by thermophilic Strand Displacement Amplification.

26. The method of claim 22 wherein the target sequence is amplified by the Polymerase Chain Reaction.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

TAGAGTCTTC AAATATCAGA GCTTTACCTA ACAA 34

( 2 ) INFORMATION FOR SEQ ID NO:2:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

ATCCGTATGG TGGATAACGT CTTTCA 26

( 2 ) INFORMATION FOR SEQ ID NO:3:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CGATTCCGCT CCAGACTTCT CGGGTCTACT GAGATCCCCT 40

( 2 ) INFORMATION FOR SEQ ID NO:4:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

ACCGCATCGA ATGCATCTCT CGGGTAAGGC GTACTCGACC 40

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGCTGAACCG GAT         13

( 2 ) INFORMATION FOR SEQ ID NO:6:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCCACCCGCC AAC         13